United States Patent
Pomerleau et al.

(10) Patent No.: US 10,792,394 B2
(45) Date of Patent: Oct. 6, 2020

(54) METHODS FOR LOCALIZED MODIFICATION OF TISSUE PRODUCTS

(71) Applicant: LifeCell Corporation, Branchburg, NJ (US)

(72) Inventors: Ming F. Pomerleau, Califon, NJ (US); Hua Wan, Princeton, NJ (US); Hui Xu, Plainsboro, NJ (US); Dennis Y. Lee, Scotch Plains, NJ (US)

(73) Assignee: LIFECELL CORPORATION, Madison, NJ (US)

( * ) Notice: Subject to any disclaimer, the term of this patent is extended or adjusted under 35 U.S.C. 154(b) by 370 days.

(21) Appl. No.: 15/606,924

(22) Filed: May 26, 2017

(65) Prior Publication Data
US 2017/0348460 A1 Dec. 7, 2017

Related U.S. Application Data

(60) Provisional application No. 62/345,346, filed on Jun. 3, 2016.

(51) Int. Cl.
*A61L 27/36* (2006.01)
*A61K 38/39* (2006.01)

(52) U.S. Cl.
CPC ......... *A61L 27/3687* (2013.01); *A61L 27/362* (2013.01); *A61L 27/3625* (2013.01); *A61L 27/3629* (2013.01); *A61L 27/3691* (2013.01); *A61K 38/39* (2013.01); *A61L 2430/40* (2013.01)

(58) Field of Classification Search
CPC ...... A61L 27/3687; A61L 31/16; A61L 27/54; A61L 27/3691; A61L 2430/40; A61K 35/35; A61K 38/39
See application file for complete search history.

(56) References Cited

U.S. PATENT DOCUMENTS

| | | | |
|---|---|---|---|
| 4,582,640 | A | 4/1986 | Smestad et al. |
| 4,902,508 | A | 2/1990 | Badylak et al. |
| 4,969,912 | A | 11/1990 | Kelman et al. |
| 5,104,957 | A | 4/1992 | Kelman et al. |
| 5,131,850 | A | 7/1992 | Brockbank |
| 5,160,313 | A | 11/1992 | Carpenter et al. |
| 5,231,169 | A | 7/1993 | Constantz et al. |
| 5,254,133 | A | 10/1993 | Seid |
| 5,275,826 | A | 1/1994 | Badylak et al. |
| 5,284,655 | A | 2/1994 | Bogdansky et al. |

(Continued)

FOREIGN PATENT DOCUMENTS

| | | |
|---|---|---|
| CN | 1266716 A | 9/2000 |
| JP | 2004-107303 A | 4/2004 |

(Continued)

OTHER PUBLICATIONS

U.S. Appl. No. 14/162,915, filed Jan. 24, 2014, U.S. Pat. No. 9,592,254, Mar. 14, 2017.

(Continued)

*Primary Examiner* — Kara D Johnson
(74) *Attorney, Agent, or Firm* — McCarter & English, LLP (57) ABSTRACT

Methods for treating tissue matrices and tissue matrices produced according to the methods are provided. The methods can include treating select portions of a tissue matrix with a fluid containing at least one agent to produce a tissue matrix with variable mechanical and/or biological properties.

28 Claims, 12 Drawing Sheets

(56) References Cited

U.S. PATENT DOCUMENTS

| | | | |
|---|---|---|---|
| 5,332,802 A | 7/1994 | Kelman et al. | |
| 5,332,804 A | 7/1994 | Florkiewicz et al. | |
| 5,336,616 A | 8/1994 | Livesey et al. | |
| 5,364,756 A | 11/1994 | Livesey et al. | |
| 5,489,304 A | 2/1996 | Orgill et al. | |
| 5,547,681 A | 8/1996 | Clark et al. | |
| 5,613,982 A | 3/1997 | Goldstein | |
| 5,632,778 A | 5/1997 | Goldstein | |
| 5,641,518 A | 6/1997 | Badylak et al. | |
| 5,728,752 A | 3/1998 | Scopelianos et al. | |
| 5,739,176 A | 4/1998 | Dunn et al. | |
| 5,800,537 A | 9/1998 | Bell | |
| 5,893,888 A | 4/1999 | Bell | |
| 5,993,844 A | 11/1999 | Abraham et al. | |
| 6,027,743 A | 2/2000 | Khouri et al. | |
| 6,096,347 A | 8/2000 | Geddes et al. | |
| 6,113,623 A | 9/2000 | Sgro | |
| 6,166,288 A | 12/2000 | Diamond et al. | |
| 6,179,872 B1 | 1/2001 | Bell et al. | |
| 6,194,136 B1 | 2/2001 | Livesey et al. | |
| 6,326,018 B1 | 12/2001 | Gertzman et al. | |
| 6,371,992 B1 | 4/2002 | Tanagho et al. | |
| 6,381,026 B1 | 4/2002 | Schiff et al. | |
| 6,432,710 B1 | 8/2002 | Boss, Jr. et al. | |
| 6,485,723 B1 | 11/2002 | Badylak et al. | |
| 6,576,265 B1 | 6/2003 | Spievack | |
| 6,666,892 B2 | 12/2003 | Hiles et al. | |
| 6,835,385 B2 | 12/2004 | Buck | |
| 6,933,326 B1 | 8/2005 | Griffey et al. | |
| 7,022,348 B2 | 4/2006 | Ketharanathan | |
| 7,121,999 B2 | 10/2006 | Abraham et al. | |
| 7,153,518 B2 | 12/2006 | Wironen et al. | |
| 7,358,284 B2 | 4/2008 | Griffey et al. | |
| 7,425,322 B2 | 9/2008 | Cohn et al. | |
| 7,498,040 B2 | 3/2009 | Masinaei et al. | |
| 7,498,041 B2 | 3/2009 | Masinaei et al. | |
| 7,645,568 B2 | 1/2010 | Stone | |
| 7,799,767 B2 | 9/2010 | Lamberti et al. | |
| 7,838,021 B2 | 11/2010 | Lafont et al. | |
| 8,067,149 B2 | 11/2011 | Livesey et al. | |
| 8,257,372 B2 | 9/2012 | Swain et al. | |
| 8,324,449 B2 | 12/2012 | McQuillan et al. | |
| 8,415,125 B2 | 4/2013 | Fujisato et al. | |
| 8,734,409 B2 | 5/2014 | Swain et al. | |
| 9,206,442 B2 | 12/2015 | Chen | |
| 9,238,793 B2 | 1/2016 | Chen et al. | |
| 9,382,422 B2 | 7/2016 | Owens et al. | |
| 9,592,254 B2 | 3/2017 | Monteiro et al. | |
| 9,592,320 B2 | 3/2017 | Mezger et al. | |
| 2002/0103542 A1 | 8/2002 | Bilbo | |
| 2003/0035843 A1 | 2/2003 | Livesey et al. | |
| 2003/0143207 A1 | 7/2003 | Livesey et al. | |
| 2004/0037735 A1 | 2/2004 | DePaula et al. | |
| 2004/0191226 A1 | 9/2004 | Badylak | |
| 2005/0028228 A1* | 2/2005 | McQuillan | A61K 38/17 800/17 |
| 2005/0159822 A1 | 7/2005 | Griffey et al. | |
| 2006/0073592 A1 | 4/2006 | Sun et al. | |
| 2006/0127375 A1 | 6/2006 | Livesey et al. | |
| 2006/0159641 A1 | 7/2006 | Girardot et al. | |
| 2006/0210960 A1 | 9/2006 | Livesey et al. | |
| 2006/0272102 A1 | 12/2006 | Liu et al. | |
| 2007/0009586 A1 | 1/2007 | Cohen et al. | |
| 2007/0078522 A2 | 4/2007 | Griffey et al. | |
| 2007/0104759 A1 | 5/2007 | Dunn et al. | |
| 2007/0248575 A1 | 10/2007 | Connor et al. | |
| 2008/0027542 A1 | 1/2008 | McQuillan et al. | |
| 2008/0027562 A1 | 1/2008 | Fujisato et al. | |
| 2009/0035289 A1 | 2/2009 | Wagner et al. | |
| 2009/0130221 A1 | 5/2009 | Bolland et al. | |
| 2009/0239809 A1 | 9/2009 | Chen et al. | |
| 2009/0306790 A1 | 12/2009 | Sun | |
| 2010/0021961 A1 | 1/2010 | Fujisato et al. | |
| 2010/0040687 A1 | 2/2010 | Pedrozo et al. | |
| 2010/0209408 A1 | 8/2010 | Stephen et al. | |
| 2010/0233235 A1 | 9/2010 | Matheny et al. | |
| 2010/0272782 A1 | 10/2010 | Owens et al. | |
| 2011/0020271 A1 | 1/2011 | Niklason et al. | |
| 2011/0021753 A1 | 1/2011 | Huang | |
| 2012/0010728 A1 | 1/2012 | Sun et al. | |
| 2012/0040013 A1 | 2/2012 | Owens et al. | |
| 2012/0252065 A1 | 10/2012 | Rozenszain et al. | |
| 2012/0263763 A1 | 10/2012 | Sun et al. | |
| 2012/0276213 A1 | 11/2012 | Chen | |
| 2012/0310367 A1 | 12/2012 | Connor | |
| 2013/0013068 A1 | 1/2013 | Forsell et al. | |
| 2013/0053960 A1 | 2/2013 | Park et al. | |
| 2013/0121970 A1 | 5/2013 | Owens et al. | |
| 2013/0158676 A1 | 6/2013 | Hayzlett et al. | |
| 2014/0004549 A1 | 1/2014 | Chen et al. | |
| 2014/0220095 A1* | 8/2014 | Monteiro | A61K 35/12 424/423 |
| 2014/0377833 A1 | 12/2014 | Chen et al. | |

FOREIGN PATENT DOCUMENTS

| | | |
|---|---|---|
| WO | 1999/065470 A1 | 12/1999 |
| WO | 2004/020470 A1 | 3/2004 |
| WO | 2014/123703 A1 | 8/2014 |
| WO | 2015/035115 A1 | 3/2015 |

OTHER PUBLICATIONS

U.S. Appl. No. 15/419,076, filed Jan. 30, 2017, Non-Published.

Ahn et al., "The past, present, and future of xenotransplantation" Yonsei Med J., 45(6):1017-1024 (Dec. 31, 2004).

Allman et al., "Xenogeneic Extracellular Matrix Grafts Elicit a TH2-Restricted Immune Response" Transplantation, 71(11):1631-1640 (Jun. 15, 2001).

Aycock et al., "Parastomal Hernia Repair With Acellular Dermal Matrix" J. Wound Ostomy Continence Nurs., 34(5):521-523 (2007).

Badylak et al., "Endothelial cell adherence to small intestinal submucosa: An acellular bioscaffold" Biomaterials, 20:2257-2263 (1999).

Badylak et al., "Extracellular Matrix as a Biological Scaffold Material: Structure and Function" Acta Biomaterialia, 5(1):1-13 (2009).

Beniker et al., "The use of acellular dermal matrix as a scaffold for periosteum replacement" Orthopedics, 26(5 Suppl):s591-s596 (May 2003).

Bruder et al., "The Effect of Implants Loaded with Autologous Mesenchymal Stem Cells on the Healing of Canine Segmental Bone Defects" J. Bone Joint Surg., 80:985-986 (1998).

Buma et al., "Tissue engineering of the meniscus" Biomaterials, 25(9):1523-1532 (2004).

Chaplin et al., "Use of an Acellular Dermal Allograft for Dural Replacement: An Experimental Study" Neurosurgery, 45(2):320-327 (Aug. 1999).

Chen et al. "Acellular Collagen Matrix as a Possible 'Off the Shelf' Biomaterial for Urethral Repair" Urology, 54(3):407-410 (1999).

Collins et al., "Cardiac xenografts between primate species provide evidence for the importance of the ?-galactosyl determinant in hyperacute rejection" J. Immunol., 154:5500-5510 (1995).

Costantino et al., "Human Dural Replacement With Acellular Dermis: Clinical Results and a Review of the Literature" Head & Neck, 22:765-771 (Dec. 2000).

Dobrin et al., "Elastase, collagenase, and the biaxial elastic properties of dog carotid artery" Am. J. Physiol. Heart Circ. Physiol., 247:H124-H131 (1984).

Edel, "The use of a connective tissue graft for closure over an immediate implant covered with occlusive membrane" Clin. Oral Implants Res., 6:60-65 (1995) (Abstract).

Fowler et al., "Ridge Preservation Utilizing an Acellular Dermal Allograft and Demineralized Freeze-Dried Bone Allograft: Part II. Immediate Endosseous Impact Placement" J. Periodontol., 71:1360-1364 (2000).

Fowler et al., "Root Coverage with an Acellular Dermal Allograft: A Three-Month Case Report" J. Contemp. Dental Pract., 1(3):1-8 (2000).

(56) References Cited

OTHER PUBLICATIONS

Galili et al., "Man, Apes, and Old World Monkeys Differ from Other Mammals in the Expression of ?-Galactosyl Epitopes on Nucleated Cells" J. Biol. Chem., 263(33):17755-17762 (1988).

Galili et al., "Interaction Between Human Natural Anti-?-Galactosyl Immunoglobulin G and Bacteria of the Human Flora" Infect. Immun., 56(7):1730-1737 (1988).

Galili et al., "Interaction of the Natural Anti-Gal Antibody with ?-Galactosyl Epitopes: a Major Obstacle for Xenotransplantation in Humans" Immunology Today, 14(10):480-482 (1993).

Gamba et al. "Experimental abdominal wall defect repaired with acellular matrix" Pediatr. Surg. Int., 18:327-331 (2002).

Gebhart et al., "A radiographical and biomechanical study of demineralized bone matrix implanted into a bone defect of rat femurs with and without bone marrow" Acta Orthop. Belg., 57(2):130-143 (1991) (Abstract).

Greenstein et al., "Parastomal Hernia Repair Using Cross-Linked Porcine Dermis: Report of a Case" Surg. Today, 38:1048-1051 (2008).

Griffey et al., "Particulate Dermal Matrix as an Injectable Soft Tissue Replacement Material" J. Biomed. Mater. Res. (Appl. Biomater. ), 58(1):10-15 (2001).

Harris, "A Comparative Study of Root Coverage Obtained with an Acellular Dermal Matrix Versus a Connective Tissue Graft: Results of 107 Recession Defects in 50 Consecutively Treated Patients" Int. J. Periodontics Restorative Dentist., 20(1):51-59 (2000).

Harris, "Root Coverage With a Connective Tissue With Partial Thickness Double Pedicle Graft and an Acellular Dermal Matrix Graft: A Clinical and Histological Evaluation of a Case Report" J. Periodontol., 69:1305-1311 (1998).

Kish et al., "Acellular Dermal Matrix (AlloDerm): New Material in the Repair of Stoma Site Hernias" The American Surgeon, 71:1047-1050 (Dec. 2005).

Kridel et al., "Septal Perforation Repair with Acellular Human Dermal Allograft" Arch. Otolaryngol. Head Neck Surg., 124:73-78 (Jan. 1998).

Laidlaw et al., "Tympanic Membrane Repair With a Dermal Allograft" Laryngoscope, 111:702-707 (Apr. 2001).

Lee et al., "In vitro evaluation of a poly(lactide-co-glycolide)-collagen composite scaffold for bone regeneration" Biomaterials, 27:3466-3472 (2006).

Lu et al., "Novel Porous Aortic Elastin and Collagen Scaffolds for Tissue Engineering" Biomaterials, 25(22):5227-5237 (2004).

Simon et al., "Early failure of the tissue engineered porcine heart valve SYNERGRAFT™ in pediatric patients" Eur. J. Cardiothorac. Surg., 23(6):1002-1006 (2003).

Zheng et al. "Porcine small intestine submucosa (SIS) is not an acellular collagenous matrix and contains porcine DNA: Possible implications in human implantation" J. Biomed. Mater. Res. B: Appl. Biomater., 73(1):61-67 (2005).

International Search Report and Written Opinion, dated Jul. 16, 2014, for International Patent Application No. PCT/US2014/012854.

Hamadeh et al., "Human natural anti-Gal IgG regulates alternative complement pathway activation on bacterial surfaces," J. Clin. Invest. 89:1223-1235 (1992).

Ionescu et al., "Effect of Papain and Bromelin on Muscle and Collagen Proteins in Beef Meat," The Annals of the University Dunarea de Jos of Galati. Fascicle VI, Food Technology, New Series, pp. 9-16, 2008.

Karlinsky et al., "In Vitro Effects of Elastase and Collagenase on Mechanical Properties of Hamster Lungs," Chest, 69(2):275-276 (1976).

Reihsner et al., "Biomechanical properties of elastase treated palmar aponeuroses," Connective Tissue Research, 26:77-86 (1991).

Tedder et al., "Stabilized Collagen Scaffolds for Heart Valve Tissue Engineering," Tissue Engineering: Part A, pp. 1-12 (2008).

Xu, "A Porcine-Derived Acellular Dermal Scaffold that Supports Soft Tissue Regeneration: Removal of Terminal Galactose-?-(1,3)-Galactose and Retention of Matrix Structure," Tissue Engineering, vol. 15, 1-13 (2009).

Yuan et al., "Effects of collagenase and elastase on the mechanical properties of lung tissue strips," J. App. Physiol., 89:3-14 (2000).

Galie, Peter A., and Jan P. Stegemann. "Simultaneous application of interstitial flow and cyclic mechanical strain to a three-dimensional cell-seeded hydrogel." Tissue Engineering Part C: Methods 17.5 (Feb. 2011): 527-536.

International Preliminary Report on Patentability for Application No. PCT/US2017/034651, dated Dec. 13, 2018, 8 pages.

Inntemational Search Report and Written Opinion issued in International Patent Application No. PCT/US2017/034651 dated Aug. 11, 2017 (13 pages).

* cited by examiner

METHODS FOR LOCALIZED MODIFICATION OF TISSUE PRODUCTS

This application claims priority under 35 USC § 119 to U.S. Provisional Patent Application No. 62/345,346, which was file on Jun. 3, 2016 and is herein incorporated by reference in its entirety.

The present disclosure relates to tissue matrices, and more particularly, to methods for localized modification of mechanical and/or biological properties of tissue matrices.

Various tissue-derived products are used to regenerate, repair, or otherwise treat diseased or damaged tissues and organs. Such products can include intact tissue grafts or acellular or reconstituted acellular tissues (e.g., acellular tissue matrices from skin, intestine, or other tissues, with or without cell seeding). Such products generally have mechanical properties determined by the tissue source (i.e., tissue type and animal from which it originated) and the processing parameters used to produce the tissue products.

Since tissue products are often used for surgical applications and/or tissue replacement or augmentation, the mechanical and biological properties of the tissue products are important. For example, tissue products must be able to provide suitable mechanical support (e.g., to close a tissue defect), while allowing tissue in-growth and regeneration. In some cases, however, it may be desirable to modify the mechanical and/or biological properties of tissue products. Furthermore, in order to improve the performance of tissue products for specific applications, it may be desirable to produce tissue products that have variable mechanical or biological properties. Accordingly, the present disclosure provides devices and methods for localized modification of mechanical or biological properties of tissue products, including acellular tissue matrices.

SUMMARY

According to various embodiments, a method for modifying a tissue matrix is provided. The method can comprise selecting a collagen-containing tissue matrix and providing a hydrophilic material having a shape corresponding to a desired pattern. The method can further comprise applying to the hydrophilic material a fluid containing at least one agent capable of modifying the collagen-containing tissue matrix and contacting the collagen-containing tissue matrix with the hydrophilic material to bring select regions of the collagen-containing tissue matrix into contact with the hydrophilic material and the fluid.

According to various embodiments, a method for modifying a tissue matrix is provided. The method can comprise selecting a collagen-containing tissue matrix and providing a material having a shape corresponding to a desired pattern. The method can further comprise applying to the material a fluid containing at least one agent capable of modifying the collagen-containing tissue matrix and contacting the collagen-containing tissue matrix with the material to bring select regions of the collagen-containing tissue matrix into contact with the material and the fluid.

In some embodiments, the tissue matrix is an acellular tissue matrix. In certain embodiments, the tissue matrix comprises a dermal tissue matrix. In other embodiments, the tissue matrix is derived from a tissue selected from fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, muscle (including skeletal, cardiac, or smooth muscle) and intestinal tissue.

In certain embodiments, the material is placed on top of the collagen-containing tissue matrix. The method can comprise applying a vertical force on the material. In other embodiments, the collagen-containing tissue matrix is placed on top of the material. The method can comprise applying a vertical force to the collagen-containing tissue matrix.

In some embodiments, the material forms at least one of a serpentine pattern, a web-like pattern, a circular pattern, a grid pattern, and a linear pattern.

In some embodiments, the at least one agent can comprise at least one of gluteraldehyde and 1-Ethyl-3-[3-dimethyl-aminopropyl]carbodiimide hydrochloride (EDC). In certain embodiments, the at least one agent can comprise a cross-linking agent. In some embodiments, the fluid can comprise an enzyme. In other embodiments the enzyme is selected from bromelain, papain, ficin, actinidin, alcalase, trypsin, dispase or combinations thereof.

In various embodiments, tissue products produced according to any of the disclosed methods are provided.

In certain embodiments, a tissue product is provided. The tissue product can comprise an acellular tissue matrix derived from a collagen-containing tissue, wherein the acellular tissue matrix comprises a flexible sheet, and wherein the tissue matrix comprises select regions wherein mechanical or biological properties of the acellular tissue matrix vary across the flexible sheet.

DESCRIPTION OF CERTAIN EXEMPLARY EMBODIMENTS

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any ranges described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

As used herein "tissue product" will refer to any human or animal tissue that contains extracellular matrix proteins. "Tissue products" can include acellular or partially decellularized tissue matrices, as well as decellularized tissue matrices that have been repopulated with exogenous cells.

Various human and animal tissues can be used to produce products for treating patients. For example, various tissue products are available for regeneration, repair, augmentation, reinforcement, and/or treatment of human tissues that have been damaged or lost due to various diseases and/or structural damage (e.g., from trauma, surgery, atrophy, and/or long-term wear and degeneration). Such products can include, for example, acellular tissue matrices, tissue allografts or xenografts, and/or reconstituted tissues (i.e., at least partially decellularized tissues that have been seeded with cells to produce viable materials).

For surgical applications, it is often desirable to produce tissue products that have certain mechanical properties. For example, the tissue product, which may include a sheet of material, should possess sufficient strength to withstand stresses during the intended use. Certain tissue products may be used to repair defects (e.g., hernias), to support surrounding tissues or implants (e.g., for breast augmentation and/or reconstruction), or to replace damaged or lost tissue (e.g., after trauma or surgical resection). Whatever the particular use, the tissue product should have sufficient strength, elasticity, and/or other mechanical properties to function until tissue regeneration and/or repair occurs.

Some tissue products, however, may be functionally improved by altering the mechanical properties of the products. For example, a number of acellular tissue matrix products are available, and often, such tissue matrices are in the form of a flexible sheet of material that has substantially uniform mechanical and/or biological properties over its entire surface area. For some indications, however, it may be desirable to alter the mechanical and/or biological properties of such tissue matrices such that the properties vary across the material. As used herein, "across the material" can include along a length or width of the material, or can include a gradient or variation in a property within the material (e.g., a gradient or variation across the depth of a sheet). For example, in some embodiments, it may be desirable to strengthen, stiffen, weaken, or make more pliable select regions of a tissue product to produce a product having variable mechanical properties. In addition, in some embodiments, it may be desirable to modify certain elastic or viscoelastic properties of a tissue matrix, including, for example, the resistance to stretching at low deformation levels (e.g., toe-region mechanics).

It may be desirable to treat select regions of the tissue products to control the rate of degradation, cell in-growth, and/or vascularization after implantation. It is known that cross-linking can increase the resistance of tissue matrices to degradation by inflammatory cells within the body, and such increased resistance can slow the rate of weakening after implantation. Accordingly, in some embodiments, it may be desirable to provide localized cross-linking to produce areas of the tissue matrix that maintain their ability to provide mechanical support at an implantation site for longer times after implantation, while simultaneously providing sufficient tissue matrix mass to support normal tissue regeneration within uncross-linked portions of the tissue matrix.

The present disclosure provides methods for treating tissues to provide variable mechanical and/or biological properties along the length, width, or thickness of a tissue matrix. The disclosure also provides tissue products produced using the methods. It will be understood that variations in biological properties can include variations or changes to the tissue product itself (e.g., by enzymatic change or chemical change), and can include variation in biologic properties due to selective application of various agents (discussed below, but including, for example, anti-microbials, anti-biotics, growth factors, anti-inflammatory agents, etc.)

According to various embodiments, a method for treating a tissue matrix is provided. The method can comprise selecting a collagen-containing tissue matrix and providing a material having a shape corresponding to a desired pattern and applying to the material a fluid containing at least one agent capable of modifying the collagen-containing tissue matrix to produce a tissue matrix having mechanical and/or biological properties that vary across the tissue matrix.

In certain embodiments, tissue matrices can be treated to provide localized variation in mechanical and/or biological properties by contacting the tissue matrices with one or more cross-linking agents and/or proteolytic enzymes. Generally, the matrices can be treated by contacting selected regions of the tissue matrices with a material containing a fluid that contains the agent or enzyme under conditions (e.g., temperature and/or pH) and for a time sufficient to produce a desired degree of cross-linking and/or proteolysis. Furthermore, in the case of application of therapeutic agents, the process can be performed under conditions and for a time to produce the desired variation in the distribution of the agent—e.g., to provide a desired variation in the concentration of the agent across a thickness of a product, or to selectively coat portions or sides of a product with the selected agent.

Figure 1A:
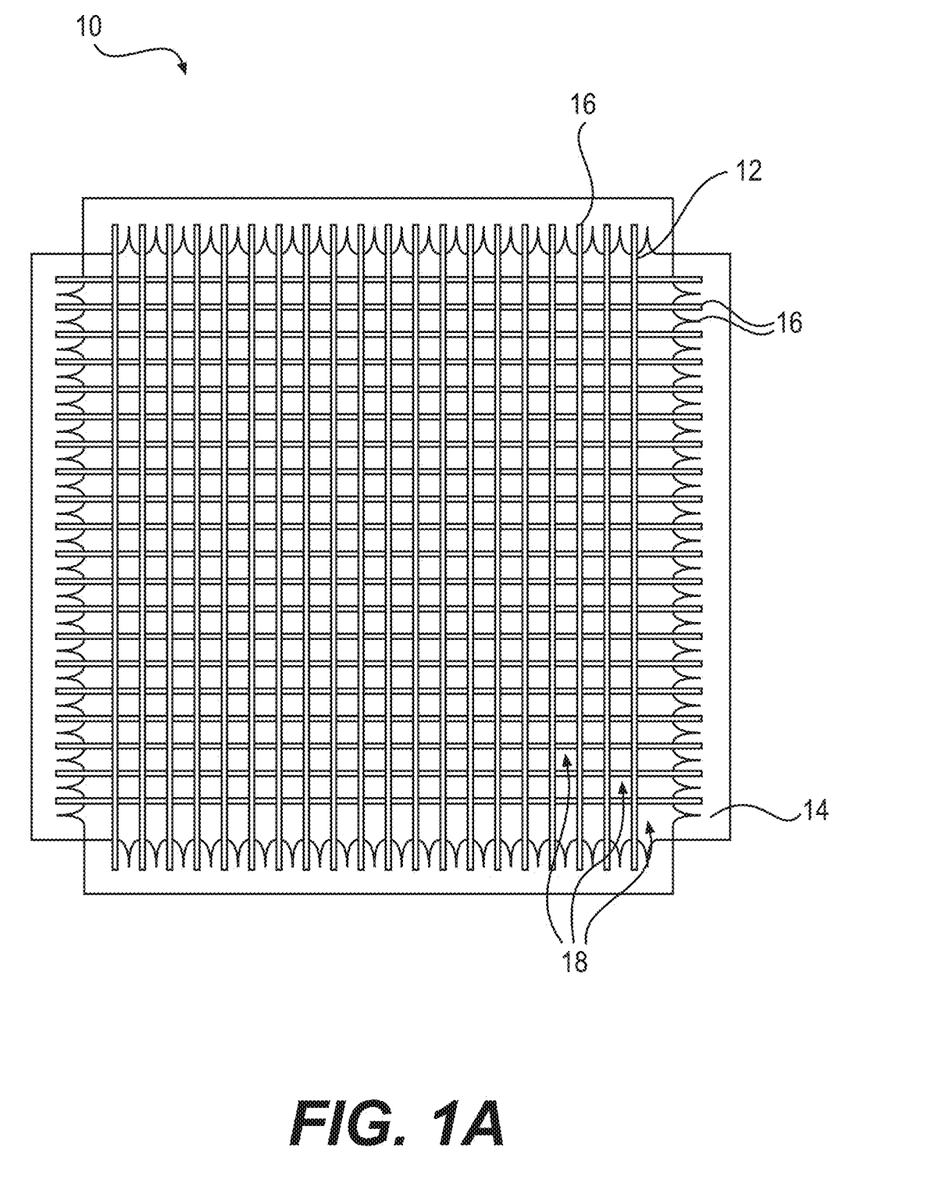
FIGS. 1A-1B illustrate a device for microfluidic modification of a tissue product, according to certain embodiments.
Figure 1B:
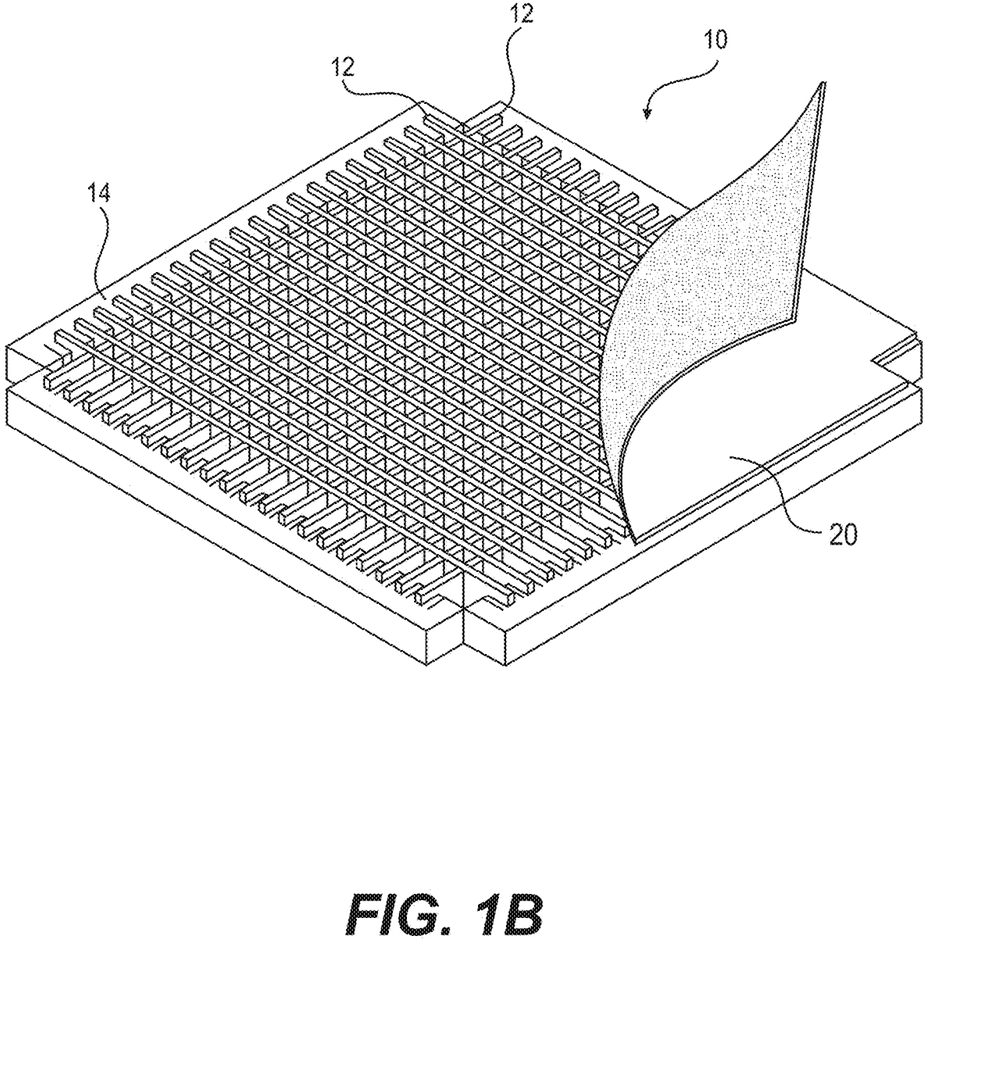
Figure 2:
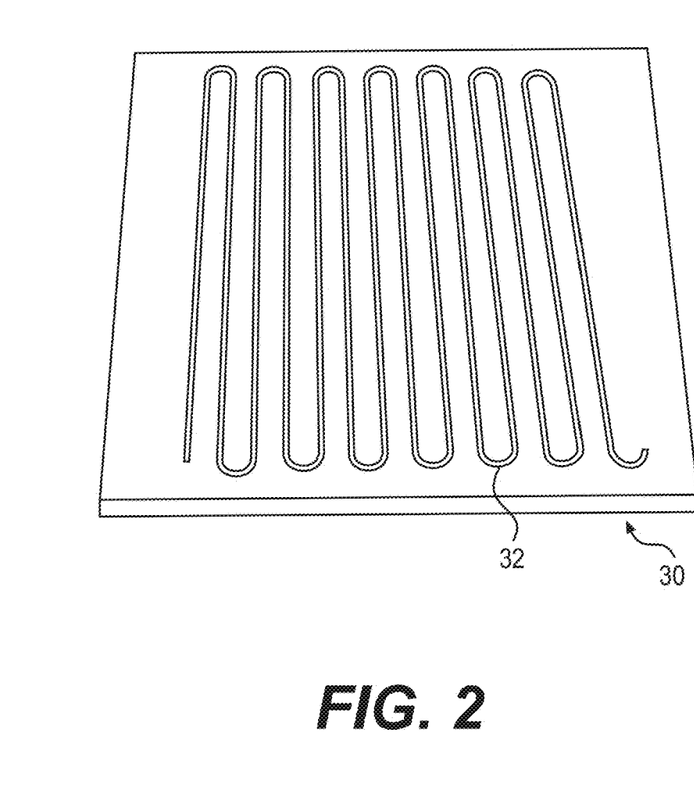
FIG. 2 provides a schematic illustration of an acellular tissue matrix that has been treated to provide localized modification of mechanical and/or biological properties, according to certain embodiments.
Figure 3:
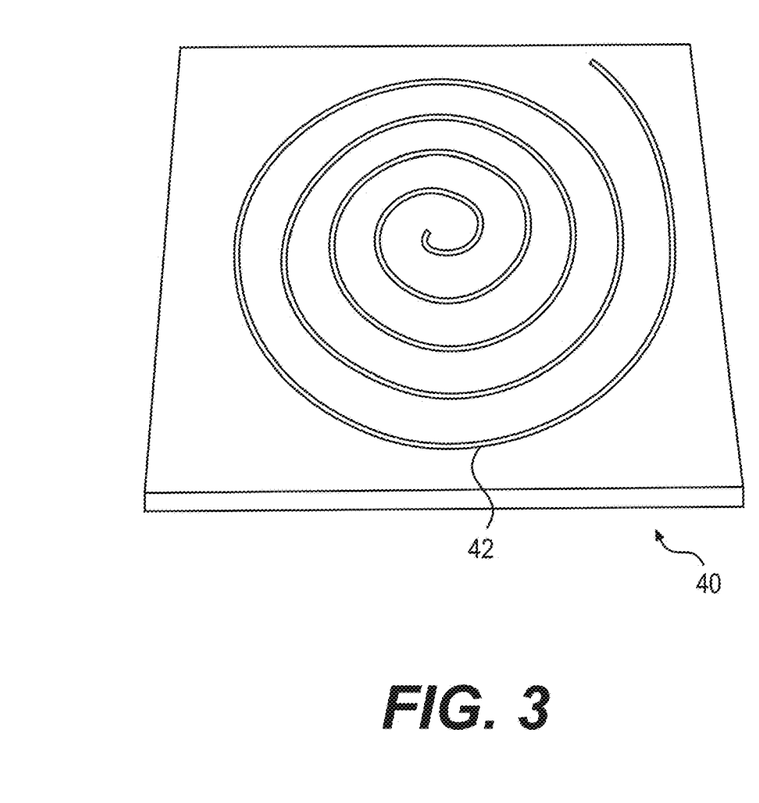
FIG. 3 provides a schematic illustration of an acellular tissue matrix that has been treated to provide localized modification of mechanical and/or biological properties, according to certain embodiments.
Figure 4:
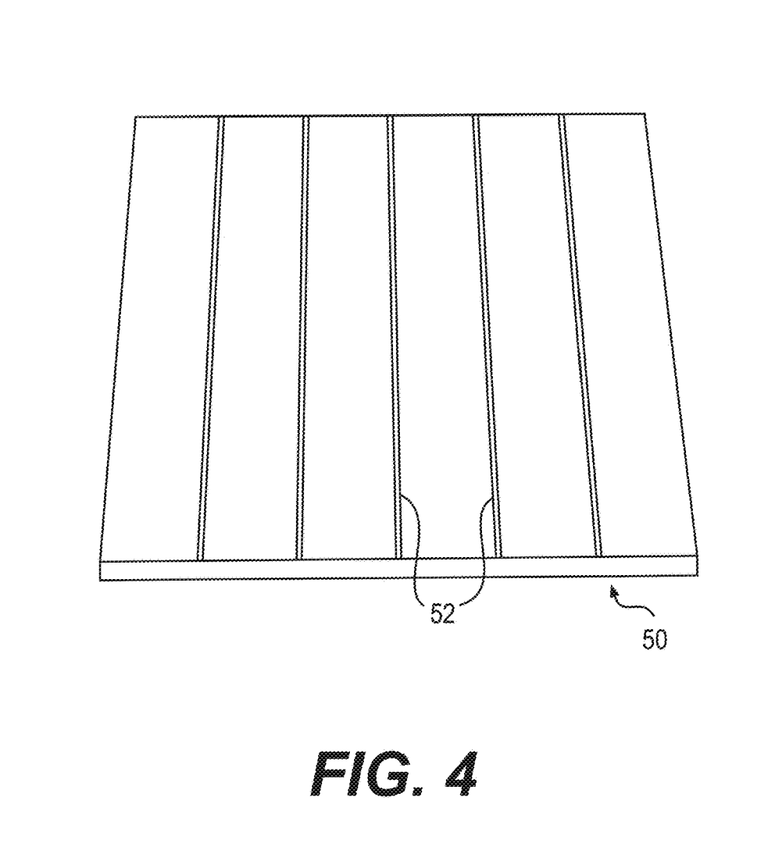
FIG. 4 provides a schematic illustration of an acellular tissue matrix that has been treated to provide localized modification of mechanical and/or biological properties, according to certain embodiments.
Figure 5:
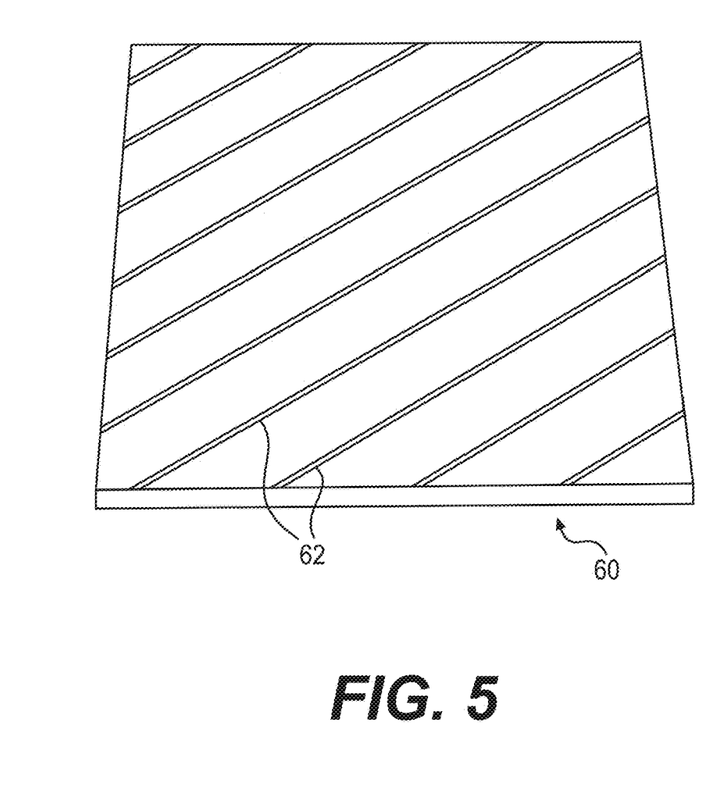
FIG. 5 provides a schematic illustration of an acellular tissue matrix that has been treated to provide localized modification of mechanical and/or biological properties, according to certain embodiments.
Figure 6:
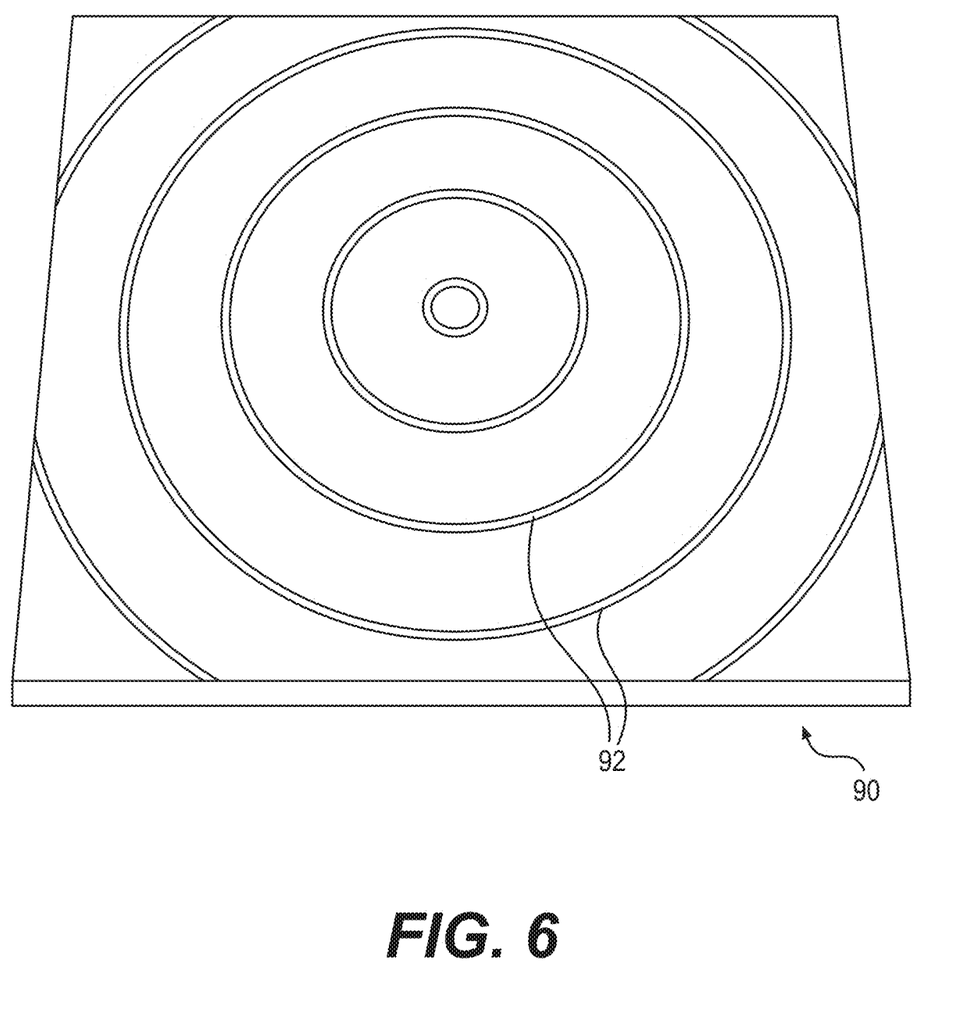
FIG. 6 provides a schematic illustration of an acellular tissue matrix that has been treated to provide localized modification of mechanical and/or biological properties, according to certain embodiments.
Figure 7:
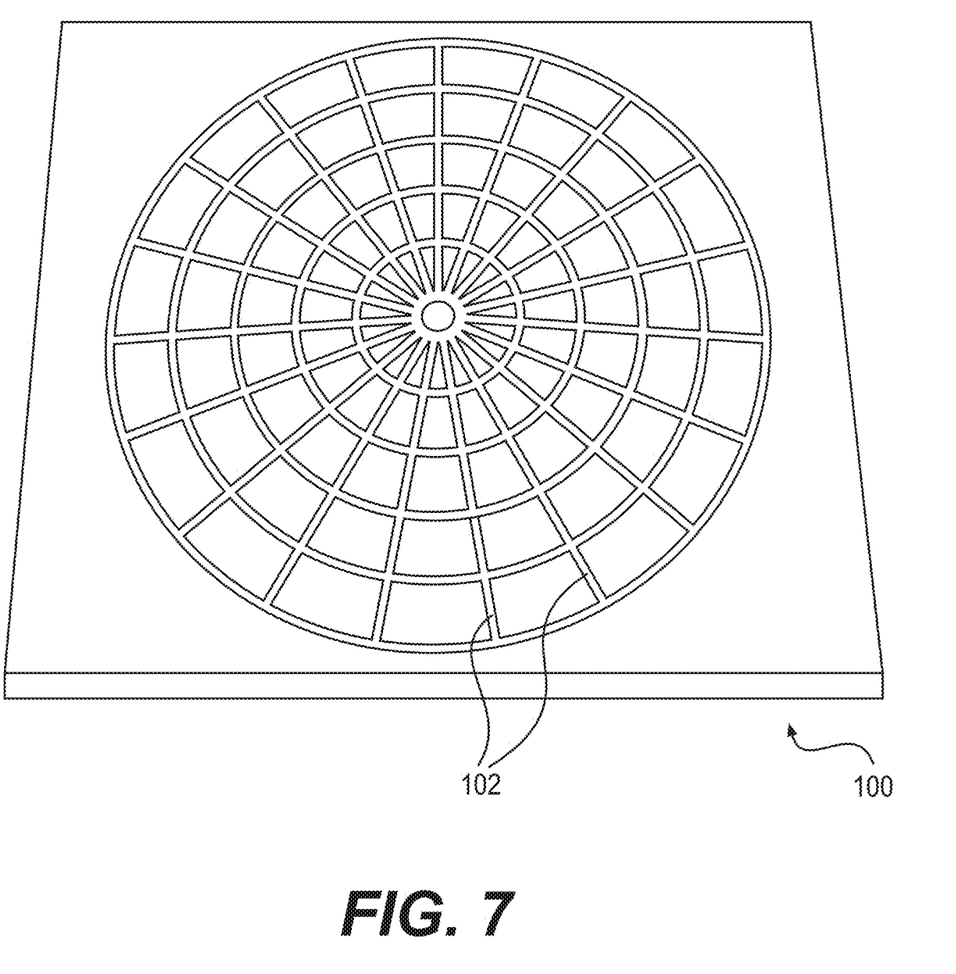
FIG. 7 provides a schematic illustration of an acellular tissue matrix that has been treated to provide localized modification of mechanical and/or biological properties, according to certain embodiments.

Specific embodiments of the devices and methods disclosed herein are illustrated in the figures. FIGS. 1A-1B illustrate a treatment device 10, including a material 12. As shown, the material 12 includes a pre-formed pattern, in this case a grid-like pattern, corresponding to a desired shape and size of selected regions to be modified in a tissue matrix.

As noted above, the device 10 can allow application of a fluid containing one or more agents capable of modifying a collagen-containing tissue matrix. The fluid can include an aqueous solvent, such as a saline buffer, phosphate buffered saline, or other suitable buffers or solutions selected to permit desired activities of the agents contained in the fluid. For example, the fluid can include a buffer with appropriate pH, salt concentrations, metal ions, or other substances needed to produce a desired activity of an enzyme or to facilitate cross-linking or other chemical modification.

The shape and configuration of the material can be selected to allow contact with only portions of a tissue matrix desired to be modified. For example, the tissue matrix can include a sheet or sheet-like material 20 (FIG. 1B) that can be placed on top of the material 12 to make contact with struts or extensions 16, while not making contact with openings 18. Accordingly, the fluid contained in the material will be contacted with and allowed to pass, to the extent desired, into the tissue matrix, thereby allowing the desired modifications (enzymatic modification, cross-linking, or other chemical modifications).

The material 12 can be supported with a frame 14 or similar base to produce a desired shape and to provide a reservoir for fluid, if needed. The frame 14 can be substantially rigid and produced from various materials such as metals, alloys, substantially rigid polymers, or any other suitable material.

The material 12 can include a variety of polymers or other suitable materials. For example, suitable materials can include polyethylene, polyester, polypropylene, and cellulose (e.g., cellulose filter paper). The material 12 can also be selected from multi component materials, such as a polymer and cellulose sponge combination or polymer with felt fabrics. Depending on the desired modification of the tissue matrix, the porosity of the material 12 can vary. The material 12 can have pore sizes between 50 to 500 microns. In addition, desirably, the material is autoclavable or otherwise sterilizable.

The material 12 can include a variety of configurations to allow it to pass a desired amount of the fluid into contact with or into the tissue to be modified. For example, the material 12 can include a hydrophilic material that will absorb or otherwise hold fluid and/or cause the fluid to be passed or transferred into the tissue material 20 (e.g., by wicking, chromatographic action, or other processes). Further, the material 12 can include other configurations such that, even if not produced from a substance that is itself hydrophilic, will allow passage of the fluid into the material to be modified. For example, the material 12 can include hydrophilic or non-hydrophilic substances that may be porous or have other micro or macrostructures to allow passage of the fluid. Such structures can include small channels or pores that allow wicking or holding of a desired fluid.

A number of different cross-linking agents, enzymes, or therapeutic agents can be used to treat the tissue matrices. For example, suitable cross-linking agents can include glutaraldehyde, 1-Ethyl-3-[3-dimethylaminopropyl] carbodiimide hydrochloride (EDC), hexamethylene diisocyanate, genepin, aldehydes, and/or lysyl oxidase; and suitable enzymes can include sulfhydryl proteases such as bromelain. In addition, the enzymes can include bromelain, alcalase, trypsin, papain, ficin, actinidin, or combinations thereof. The enzymes and cross-linking agents can be purchased commercially or obtained by purification from biologic sources.

In addition or in the alternative to enzymes or cross-linking agents, the fluids used can include other agents. For example, the devices and methods described herein can be used for focal coating (e.g., with growth factors); for focal application of drugs such as antimicrobials, antibiotics, anti-inflammatory agents, steroids, chemotherapeutic agents, immune-modulating drugs, or other substances; or focal chemical modification, e.g., to chemically bond agents for subsequent chemical reactions or to allow subsequent binding of secondary molecules. It will be understood that focal application can include a gradient or variation across the depth or thickness of a material, such as a sheet. As such, the material 12 can include a flat material that conforms to the shape of a sheet to allow application of agents to one side, thereby allowing production of a higher concentration of the agent on one side of the sheet, or a higher degree of cross-linking, enzymatic, or chemical modification on one side.

The enzymes can be contacted with the tissues to increase the pliability of the tissue without causing undesirable degradation in other mechanical and/or biological properties. For example, when a batch of tissue products is produced with or without the enzyme treatments discussed herein, the enzyme treatments will not produce an undesirable change in at least one of tensile strength, tear strength, suture strength, creep resistance, collagenase susceptibility, glycosaminoglycan content, lectin content, burst strength, thermal transition temperature, or combinations thereof. In some cases, an undesirable change is a statistically significant reduction any one of tensile strength, tear strength, suture strength, creep resistance, glycosaminoglycan content, lectin content, burst strength; an increase in collagenase susceptibility; or a change (upward or downward) in thermal transition temperature (as measure using differential scanning calorimetry).

In some cases, the enzymes are selected such that they cause site-specific cleavage of proteins within the tissues. For example, it has been found that treatment of porcine dermal materials with bromelain does not cause further alterations in the matrix structure after a certain amount of treatment. Therefore, treatment of dermis with bromelain does not cause further change in the matrix with prolonged exposure or after extended periods of time.

In addition, the enzymes and cross-linking agents can be applied to the tissues in a variety of suitable solutions. For example, bromelain has been found to be effective when applied to tissues in normal saline, but other suitable buffers (e.g., PBS) can be used.

The material 12 used to contact the tissue matrix 20 with enzymes and/or cross-linking agents can have a variety of different configurations. For example, as described in further detail below with respect to FIGS. 2-12, the tissue matrix 20 can be treated by cross-linking and/or treatment with proteolytic enzymes at a number of suitable locations to produce a pattern providing desired variations in mechanical and/or biological properties. In addition, as already mentioned, the configurations can be such that the selected agent is applied to the entire surface of a sheet or other shape, thereby allowing production of a gradient or single-sided application of whatever agent is used.

Figure 8:
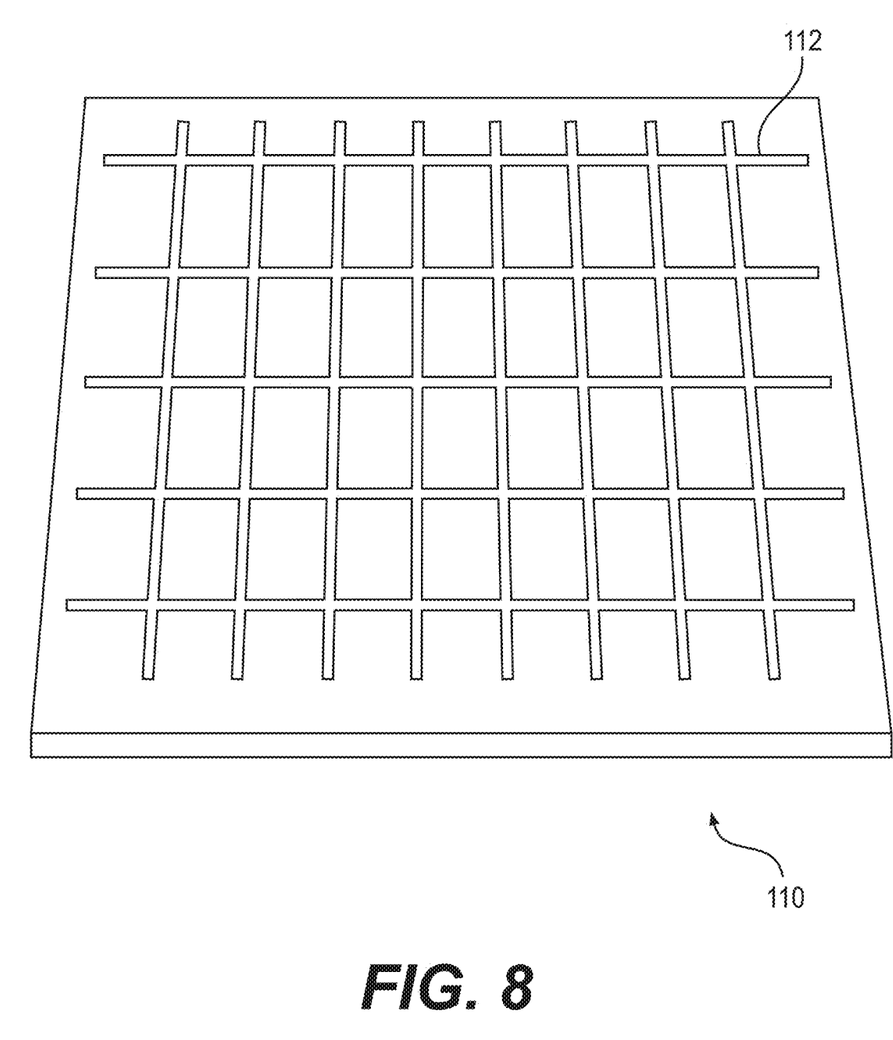
FIG. 8 provides a schematic illustration of an acellular tissue matrix that has been treated to provide localized modification of mechanical and/or biological properties, according to certain embodiments.

The methods of the present disclosure can be used to modify mechanical and/or biological properties in a number of different locations. FIGS. 2-13 illustrate acellular tissue matrices (30, 40, 50, 60, 90, 100, 110, 190, 200, 300, 400, 500) that have been treated to provide localized modification of mechanical and/or biological properties, according to certain embodiments. In various embodiments, the tissue matrices can be treated to modify select regions of a sheet-like tissue matrix over regions having a serpentine pattern 32 (FIG. 2), a spiral pattern 42 (FIG. 3), linear patterns 52, 62 (FIGS. 4 and 5), in a circular pattern 92 (FIG. 6), in a web-like pattern 102 (FIG. 7), or in a grid pattern 112 (FIG. 8).

Specific patterns or applications of localized modifications can be selected for production of devices suitable for particular surgical reasons. For example, FIG. 9 provides a schematic illustration of an acellular tissue matrix that has been treated to provide localized modification of mechanical and/or biological properties, including regions of reinforcement or modification around holes or pilot holes, while FIGS. 10-13 include devices with specific patterns selected for use in an abdominal surgery or defect repair.

Figure 9:
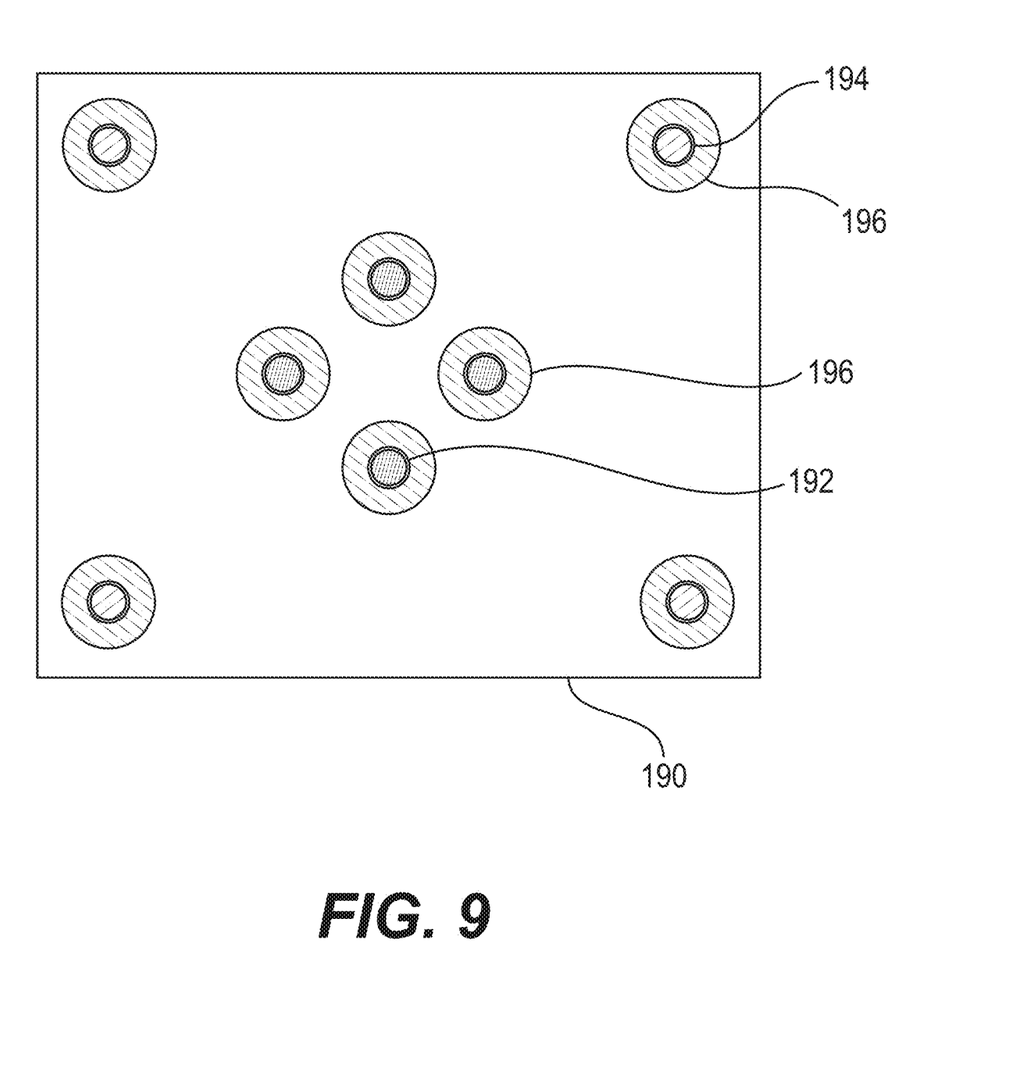
FIG. 9 provides a schematic illustration of an acellular tissue matrix that has been treated to provide localized modification of mechanical and/or biological properties, including regions of reinforcement or modification around holes or pilot holes, according to certain embodiments.

The device of FIG. 9, includes a tissue matrix 190 having holes or pilot holes 192, 194, with surrounding regions of modification 196. The holes or pilot holes may be included in tissue matrix products, for example, to allow passage of sutures, clips, or other fixation devices. The regions of modification 196 can include areas of increased cross-linking to provide reinforcement or higher suture-retention strength. In addition, the regions 196 could include other changes such as anti-inflammatory agents or anti-microbials, should there be concern about increased inflammation or infection risk around fixation devices.

The devices described herein may also be specifically designed for certain applications. For example, FIGS. 10-13 provide devices 200, 300, 400, 500 specifically designed for abdominal wall treatment, e.g., abdominal wall reinforcement or other treatment. As such, FIGS. 10-13 depict rectus abdominus muscles 214 and a mid-line abdominal incision 212. The devices 200, 300, 400, 500 can include regions 210, 310, 410, 510 of focal modification. The regions 210, 310, 410, 510 can include, for example, regions of cross-linking to support the mid-line incision and/or to assist in suture or staple retention. Further, the regions may include other modifications, such as anti-microbials.

Figure 10:
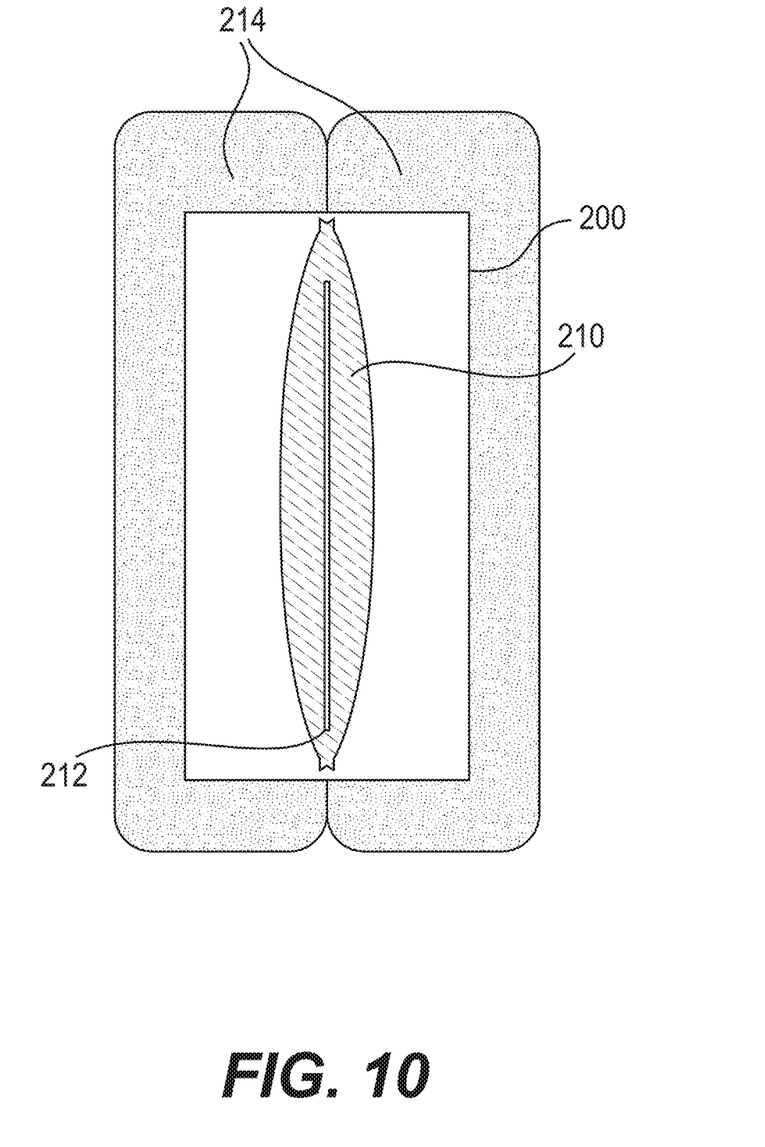
FIG. 10 provides a schematic illustration of an acellular tissue matrix that has been treated to provide localized modification of mechanical and/or biological properties, including a specific pattern for use in an abdominal surgery or defect repair, according to certain embodiments.
Figure 11:
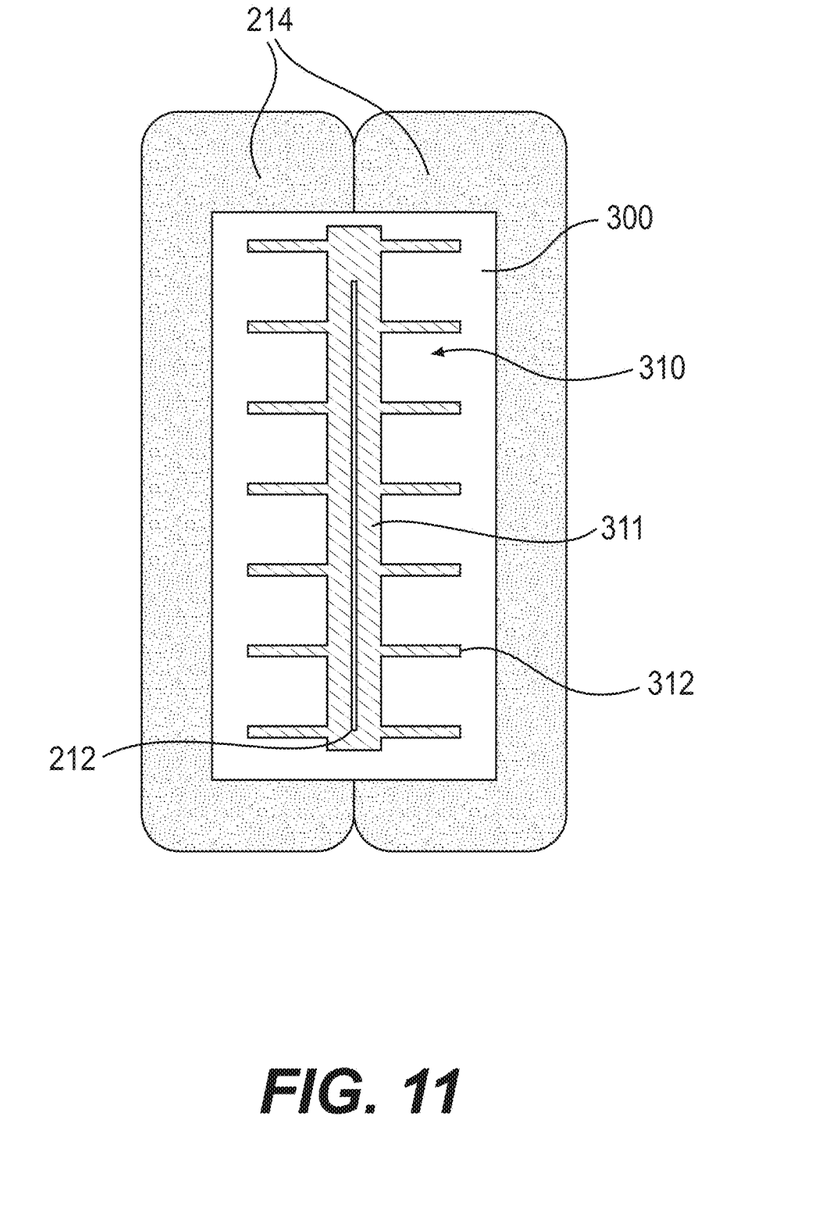
FIG. 11 provides a schematic illustration of another acellular tissue matrix that has been treated to provide localized modification of mechanical and/or biological properties, including a specific pattern for use in an abdominal surgery or defect repair, according to certain embodiments.
Figure 12:
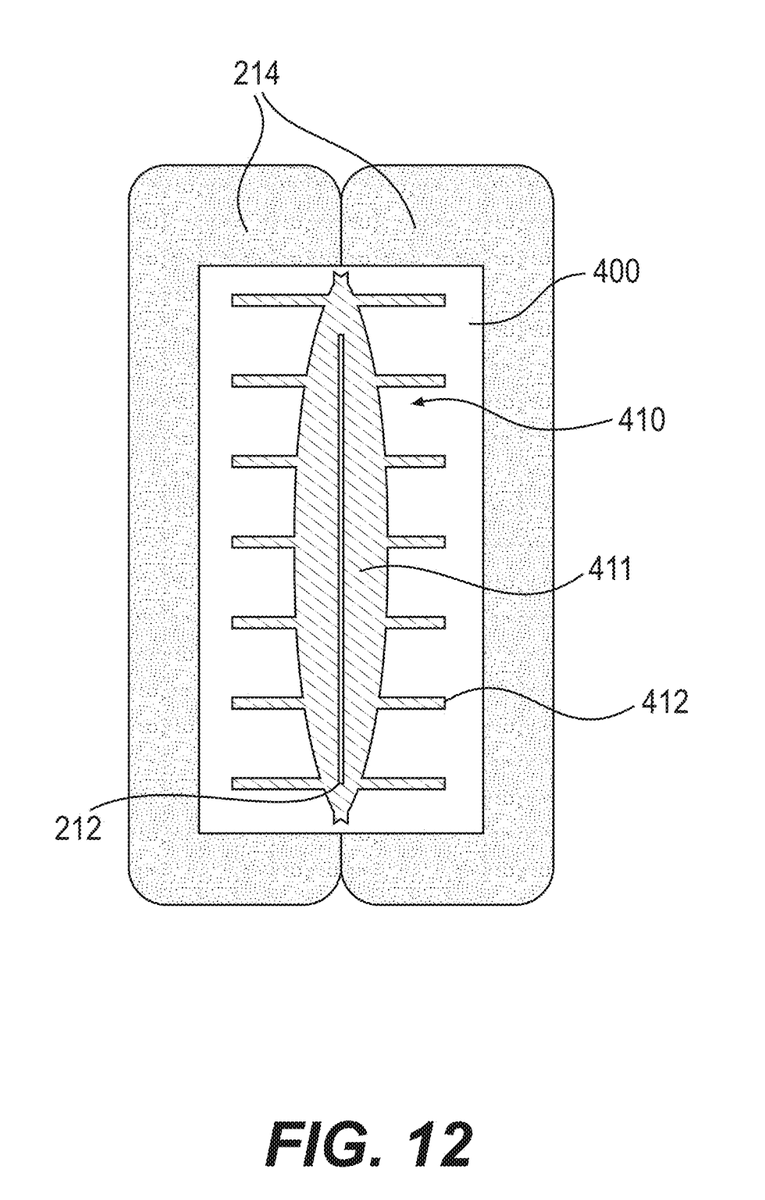
FIG. 12 provides a schematic illustration of another acellular tissue matrix that has been treated to provide localized modification of mechanical and/or biological properties, including a specific pattern for use in an abdominal surgery or defect repair, according to certain embodiments.
Figure 13:
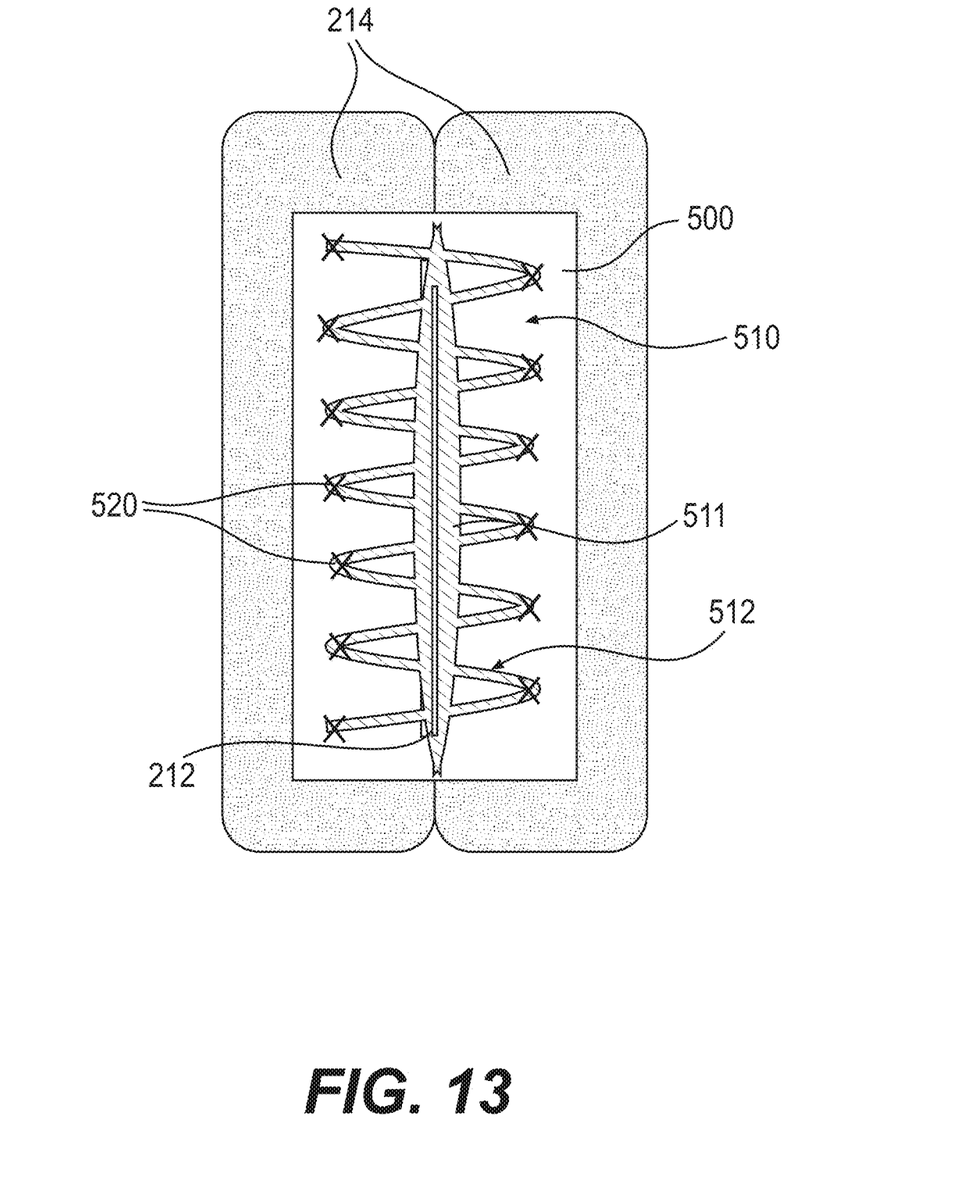
FIG. 13 provides a schematic illustration of another acellular tissue matrix that has been treated to provide localized modification of mechanical and/or biological properties, including a specific pattern for use in an abdominal surgery or defect repair, according to certain embodiments.

The devices of FIGS. 10-13 can include a number of shapes or configuration for the modifications 210, 310, 410, 510. For example, FIG. 10 provides an oblong region 210 that may be aligned with the mid-line incision 212, while FIG. 11 provides a central region 311 with extensions 312, and FIG. 12 provides an oblong region 411 with extensions 412. In addition, FIG. 13 provides an oblong region 511 with zig-zag or other appropriately shaped extensions 512.

The extensions 312, 412, 512 (and possibly the regions 210, 310, 410, 510) can provide a number of advantages. For example, the extensions 312, 412, 512 can include regions of higher stiffness, tensile strength, or other modified properties that can be directed along regions of potentially high stress or potential incision opening. In addition, the extensions can provide regions for fixation using suture 520 or other fixation devices.

The specific pattern of the region selected for localized cross-linking proteolytic treatment, or application of various agents can be selected for a variety of reasons. It is known that cross-linking can increase the resistance of tissue matrices to degradation by inflammatory cells within the body, and such increased resistance can slow the rate of weakening after implantation. Excessive cross-linking, however, can have adverse effects on cell infiltration and regeneration of normal tissue within the tissue matrix. Accordingly, in some embodiments, it may be desirable to provide localized cross-linking to provide areas of the tissue matrix that maintain their ability to provide mechanical support to an implantation site for longer times after implantation, while simultaneously providing sufficient tissue matrix mass to support normal tissue regeneration within uncross-linked portions of the tissue matrix.

Localized protease treatment may be used for a variety of reasons. For example, localized protease treatment can allow production of differing strengths or other mechanical properties. In addition, production of tissue matrices with localized pliability may be to allow a surgeon to place tissue in small openings, including passing a tissue matrix through a laparoscopic incision or trocar. In addition, production of tissue with localized pliability can be beneficial to allow matching of compliances with natural tissues or to match or align with anisotropic mechanical properties of tissues.

The specific pattern of localized treatment may be selected based on a desired implantation site or treatment method. For example, in various embodiments, the pattern may be selected to provide a treated tissue matrix having improved mechanical properties (e.g., higher yield strength) along dimensions that may be more likely to experience higher loads during use. For example, in the embodiments of FIGS. 2-8, the pattern may be selected to increase the strength of the sheet of tissue matrix along one or more axes parallel to the sheet of tissue matrix.

The concentration and specific enzyme or chemical used for cross-linking or proteolysis, as well as the type and porosity of the material can be selected for a variety of reasons. For example, in general, the specific concentration, time of exposure, and porosity of the material are selected based on the desired degree of cross-linking or proteolysis. In addition, since different enzymes and/or cross-linking agents may have proteolytic or cross-linking effects on different amino acids, combinations of two or more enzymes or cross-linking agents can be used.

The tissue products according to the present disclosure can be selected to provide a variety of different biological and/or mechanical properties. For example, an acellular tissue matrix or other tissue product can be selected to allow tissue in-growth and remodeling to assist in regeneration of tissue normally found at the site where the matrix is implanted. For example, an acellular tissue matrix, when implanted on or into fascia or other soft tissue, may be selected to allow regeneration of the fascia or other soft tissue without excessive fibrosis or scar formation. In certain embodiments, the tissue product can be formed from ALLODERM® or STRATTICE™ (LIFECELL CORPORATION, Branchburg, N.J.), which are human and porcine acellular dermal matrices respectively. Alternatively, other suitable acellular tissue matrices can be used, as described further below. The tissues can be selected from a variety of tissue sources including skin (dermis or whole skin), fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, muscle (of any type), and intestinal tissue. The methods described herein can be used to process any collagenous tissue type and for any tissue matrix product. For example, a number of biological scaffold materials are described by Badylak et al., and the methods of the present disclosure can be used to treat those or other tissue products known in the art. Badylak et al., "Extracellular Matrix as a Biological Scaffold Material: Structure and Function," Acta Biomaterialia (2008), doi:10.1016/j.actbio.2008.09.013.

In some cases, the tissue matrix can be provided as a decellularized tissue matrix. Suitable acellular tissue matrices are described further below. In other cases, the method can further include processing intact tissue to remove cells or other materials either before, after, or both before and after cross-linking or proteolytic treatment according to the present application. The tissues can be completely or partially decellularized to yield acellular tissue matrices or extracellular tissue materials to be used for patients. For example, various tissues, such as skin, intestine, bone, cartilage, nerve tissue (e.g., nerve fibers or dura), tendons, ligaments, or other tissues can be completely or partially decellularized to produce tissue products useful for patients. In some cases, these decellularized products can be used without addition of exogenous cellular materials (e.g., stem cells). In certain cases, these decellularized products can be seeded with cells from autologous sources or other sources to facilitate treatment. Suitable processes for producing acellular tissue matrices are described below.

The invention claimed is:

1. A method for modifying a tissue product, comprising:
   selecting a collagen-containing tissue product;
   providing a hydrophilic material having at least one strut having a shape corresponding to a desired pattern;
   applying to the hydrophilic material a fluid containing at least one agent capable of passing through the hydrophilic material to a top side of the hydrophilic material and modifying the collagen-containing tissue product; and
   contacting the collagen-containing tissue product with the at least one strut at the top side of the hydrophilic material to bring select regions of the collagen-containing tissue product into contact with the top side of the hydrophilic material and the fluid.

2. The method of claim 1, wherein the tissue product is an acellular tissue matrix.

3. The method of claim 2, wherein the tissue product comprises a dermal tissue matrix.

4. The method claim 2, wherein the tissue product is derived from a tissue selected from fascia adipose, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, muscle, and intestinal tissue.

5. The method of claim 1, wherein the hydrophilic material is placed on top of the collagen-containing tissue product.

6. The method of claim 5, further comprising applying a vertical force on the hydrophilic material.

7. The method of claim 1, wherein the collagen-containing tissue product is placed on top of the hydrophilic material.

8. The method of claim 7, further comprising applying a vertical force on the collagen-containing tissue product.

9. The method of claim 1, wherein the hydrophilic material forms at least one of a serpentine pattern, a web-like pattern, a circular pattern, a grid pattern, an elongated pattern, an elongated pattern with extensions, and a linear pattern.

10. The method of claim 1, wherein the at least one agent comprises at least one of glutaraldehyde and 1-Ethyl-3-[3-dimethylaminopropyl]carbodiimide hydrochloride (EDC).

11. The method of claim 1, wherein the at least one agent comprises a cross-linking agent.

12. The method of claim 1, wherein at least one agent comprises an enzyme.

13. The method of claim 12, wherein the enzyme is selected from at least one of bromelain, papain, ficin, actinidin, alcalase, trypsin, dispase or combinations thereof.

14. The method of claim 1, wherein the at least one agent includes at least one of an antimicrobial, an anti-inflammatory, or a growth factor.

15. A method for modifying a tissue product, comprising:
   selecting a collagen-containing tissue product;
   providing a material having at least one strut having a shape corresponding to a desired pattern;
   applying to the material a fluid containing at least one agent capable of passing through the material to a top side of the material and modifying the collagen-containing tissue product; and
   contacting the collagen-containing tissue product with the at least one strut at the top side of the material to bring select regions of the collagen-containing tissue product into contact with the top side of the material and the fluid.

16. The method of claim 15, wherein the tissue product is an acellular tissue matrix.

17. The method of claim 16, wherein the tissue product comprises a dermal tissue matrix.

18. The method claim 16, wherein the tissue product is derived from a tissue selected from fascia adipose, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, muscle, and intestinal tissue.

19. The method of claim 15, wherein the material is placed on top of the collagen-containing tissue product.

20. The method of claim 19, further comprising applying a vertical force on the material.

21. The method of claim 15, wherein the collagen-containing tissue product is placed on top of the material.

22. The method of claim 21, further comprising applying a vertical force on the collagen-containing tissue product.

23. The method of claim 15, wherein the material forms at least one of a serpentine pattern, a web-like pattern, a circular pattern, a grid pattern, an elongated pattern, an elongated pattern with extensions, and a linear pattern.

24. The method of claim 15, wherein the at least one agent comprises at least one of glutaraldehyde and 1-Ethyl-3-[3-dimethylaminopropyl]carbodiimide hydrochloride (EDC).

25. The method of claim 15, wherein the at least one agent comprises a cross-linking agent.

26. The method of claim 15, wherein at least one agent comprises an enzyme.

27. The method of claim 26, wherein the enzyme is selected from at least one of bromelain, papain, ficin, actinidin, alcalase, trypsin, dispase or combinations thereof.

28. The method of claim 15, wherein the at least one agent includes at least one of an antimicrobial, an anti-inflammatory, or a growth factor.

* * * * *